United States Patent
Sell et al.

(10) Patent No.: US 7,193,178 B2
(45) Date of Patent: Mar. 20, 2007

(54) METHOD AND APPARATUS FOR CONTROLLING THE HEATING OF AN OXYGEN SENSOR IN A MOTOR VEHICLE

(75) Inventors: Jeffrey A. Sell, West Bloomfield, MI (US); John W. Siekkinen, Novi, MI (US)

(73) Assignee: General Motors Corporation, Detroit, MI (US)

( * ) Notice: Subject to any disclaimer, the term of this patent is extended or adjusted under 35 U.S.C. 154(b) by 127 days.

(21) Appl. No.: 10/616,558

(22) Filed: Jul. 10, 2003

(65) Prior Publication Data

US 2005/0006368 A1    Jan. 13, 2005

(51) Int. Cl.
*B60L 1/02*    (2006.01)

(52) U.S. Cl. ............ 219/202; 219/205; 219/482; 219/497; 123/686; 324/917

(58) Field of Classification Search ........ 219/202, 219/205, 497, 494, 482, 490, 501; 205/785, 205/782; 324/717, 713; 73/1.02, 31.06; 204/425, 427; 123/697, 686; 422/88
See application file for complete search history.

(56) References Cited

U.S. PATENT DOCUMENTS

| | | | | | |
|---|---|---|---|---|---|
| 4,332,225 | A | * | 6/1982 | Cox et al. ................. 123/697 |
| 4,504,732 | A | * | 3/1985 | Bube et al. ................ 219/497 |
| 5,492,107 | A | * | 2/1996 | Furuya ...................... 123/686 |
| 5,562,815 | A | * | 10/1996 | Preidel ...................... 205/782 |
| 5,609,825 | A | * | 3/1997 | Fukaya et al. .............. 422/90 |
| 6,084,418 | A | * | 7/2000 | Takami et al. ............ 324/717 |
| 6,418,784 | B1 | * | 7/2002 | Samman et al. .......... 73/31.06 |
| 2003/0010088 | A1 | * | 1/2003 | Tomisawa ................. 73/1.02 |
| 2003/0052016 | A1 | * | 3/2003 | Lin et al. .................. 205/785 |

FOREIGN PATENT DOCUMENTS

JP        03009273    *    1/1991

* cited by examiner

*Primary Examiner*—Robin Evans
*Assistant Examiner*—Leonid Fastovsky
(74) *Attorney, Agent, or Firm*—Christopher DeVries

(57) ABSTRACT

Methods and apparatus are provided for controlling the heating of an oxygen sensor in a motor vehicle. The apparatus comprises an oxygen sensor for measuring oxygen levels in exhaust gases of a motor vehicle. The oxygen sensor comprising a heater rod, an outer electrode surrounding the heater rod, and a shell surrounding the outer electrode and configured for mounting the oxygen sensor in the motor vehicle. A first electrical connection coupled to the outer electrode and a second electrical connection coupled to the shell are configured to facilitate measurement of capacitance between the outer electrode and the shell during operation of the motor vehicle.

18 Claims, 3 Drawing Sheets

METHOD AND APPARATUS FOR CONTROLLING THE HEATING OF AN OXYGEN SENSOR IN A MOTOR VEHICLE

FIELD OF THE INVENTION

The present invention generally relates to an oxygen sensor, and more particularly relates to method and apparatus for controlling the heating of an oxygen sensor in a motor vehicle.

BACKGROUND OF THE INVENTION

Oxygen sensors are used in motor vehicles to measure oxygen in the vehicle exhaust. Measurements from the sensors aid in adjusting the operating parameters of the vehicle, and especially in adjusting the operating parameters to reduce hydrocarbon and other emissions and to improve fuel economy.

Oxygen sensors are typically mounted in the exhaust manifold and/or just after the catalytic converter. In either location the sensors are exposed to water vapor included in the exhaust gases. Oxygen sensors are designed to operate at an elevated temperature, usually with the sensing element of the sensor heated to a temperature greater than about 600° C. To achieve the elevated temperature, the oxygen sensors include a heater rod. A problem exists if a sensor is rapidly heated by the heater rod to the elevated temperature in the presence of condensed water vapor on portions of the sensor. Thermal shock resulting from heating the sensor in the presence of water condensate may cause cracking of elements in the sensor.

One solution to the problem of thermal shock in the presence of water condensate has been to delay the heating of the sensor for a predetermined length of time until the vehicle engine heats up and the engine temperature boils off the condensate. Unfortunately, it is difficult to determine the appropriate length of time delay before applying heater power. If the delay is too short, water condensate may still be present and element cracking may occur. If the delay is too long, although the problem of thermal shock can be avoided, the usefulness of the sensor is delayed because the sensor is not fully effective unless heated to the elevated temperature. The problem of thermal shock is most pronounced at vehicle start up before the exhaust system is heated to its full operating temperature. Unfortunately, the need for a properly functioning oxygen sensor is also most pronounced at start up and shortly thereafter when exhaust emissions are most problematic because the engine is cold. It is at this time that it is most important to be able to analyze the vehicle exhaust and to optimize the vehicle operating conditions based on that analysis.

Another solution to the problem of thermal shock has been to model the temperature of the skin of the exhaust pipe in the vicinity of the oxygen sensor. When this temperature exceeds the dew point, the heater power can be increased. However, it is difficult to make the models sufficiently accurate. For example, low points in the exhaust pipe well ahead of the sensor can collect or accumulate liquid water and these might not be accounted for in the model.

Accordingly, it is desirable to provide a method for calibrating and for controlling the heating of an oxygen sensor mounted in a motor vehicle to both optimize the performance of that sensor and to protect the sensor from thermal shock. In addition, it is desirable to provide an improved oxygen sensor and a system incorporating such an oxygen sensor in a motor vehicle. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

An oxygen sensor is provided for measuring oxygen levels in the exhaust gases of a motor vehicle. The oxygen sensor comprises a heater rod positioned inside an oxygen sensing element, an outer electrode surrounding the oxygen sensing element, and a shell surrounding the outer electrode and configured for mounting the oxygen sensor in the motor vehicle. A first electrical connection is coupled to the outer electrode and a second electrical connection is coupled to the shell. The first and second electrical connections are configured to facilitate measurement of capacitance between the outer electrode and the shell during operation of the motor vehicle.

A method is also provided for controlling the heating of an oxygen sensor mounted in a motor vehicle. The method comprises the steps of starting the engine of the motor vehicle, measuring capacitance between two elements of an oxygen sensor, and applying varying levels of power to a heater of the oxygen sensor in response to the measured capacitance.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Figure 1:
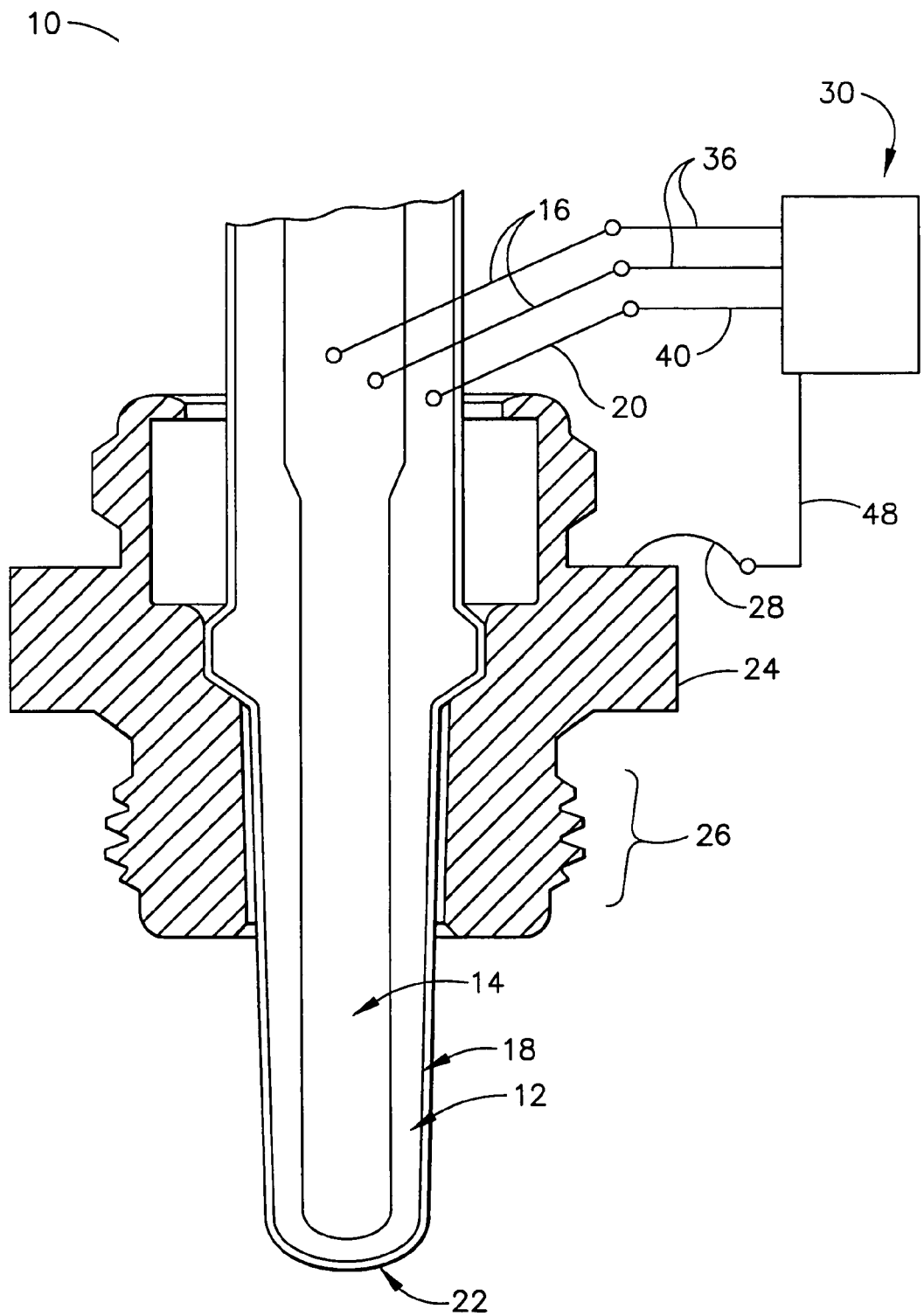
FIG. 1 illustrates, in cross section, a exemplary oxygen sensor in accordance with one embodiment of the invention.

FIG. 1 schematically illustrates, in cross section, a portion of an oxygen sensor 10 in accordance with an embodiment of the invention. The oxygen sensor includes an oxygen sensing element 12 that is of a conventional design that is well known to those of skill in the art and so need not be explained further. A heater rod 14 is positioned centrally of the sensor and inside the oxygen sensing element. Heater rod 14 includes electrical terminals 16, shown only schematically, through which electrical current can be supplied to the heater rod to cause the heater rod to heat to a desired temperature. The oxygen sensing element is surrounded by an outer electrode 18 that functions normally in the operation of sensing oxygen concentration by the oxygen sensing element. Outer electrode 18 is provided with an electrical terminal 20. The outer surface of outer electrode 18 is coated with an electrically insulating layer 22 formed, for example, from spinel, alumina, or the like. Surrounding the outer electrode is a case or shell 24. The shell is formed of a solid metal that is either cast or machined to the proper shape. Shell 24 physically supports the oxygen sensor and holds the sensor in its intended location in the vehicle, but is electrically isolated from outer electrode 18 by electrically insulating layer 22. The outer surface of shell 24 is provided with threads 26 so that the oxygen sensor can be screwed into place in the vehicle, usually either in the exhaust manifold or in the exhaust system following the catalytic converter. An electrical terminal 28 is provided on shell 24 so that electrical contact can be made to the shell. Other elements of a conventional oxygen sensor have not been illustrated. The other elements may include, for example, permeable shields, signal terminals, breathable membranes, and the like. A control module 30, remotely located from oxygen sensor 10, is coupled to the oxygen sensor by a plurality of leads. The plurality of leads include leads 36 coupled to heater rod terminals 16, lead 40 coupled to outer electrode terminal 20, and lead 48 coupled to terminal 28 on shell 24. Other leads necessary for the normal functioning of the oxygen sensors may also be coupled from the oxygen sensor to the control module.

The inventors have discovered that capacitance measured between the outer electrode and the shell provides a measure of the amount of liquid water on the oxygen sensor. The measured capacitance increases because liquid water has a higher dielectric constant than the air and/or insulating dielectric layer normally existing between the outer electrode and the shell. By monitoring the capacitance between the outer electrode and the shell of the oxygen sensor, the measured capacitance can be used to control heating of the heater rod in a manner to protect the oxygen sensor from thermal shock and yet achieve optimum sensing of the oxygen content of the exhaust gases of the vehicle. Accordingly, leads 40 and 48 couple outer electrode 18 and shell 24, respectively, to control module 30. Control module 30 can be a microprocessor, microcontroller, a portion of the engine controller, or the like. In accordance with an embodiment of the invention, control module 30, in addition to controlling the normal functioning of the oxygen sensor (such as, for example, monitoring the sensed oxygen concentration and providing that information to the engine control module), also measures the capacitance between outer electrode 18 and shell 24. The capacitance measuring function can be accomplished, for example, by configuring the control module with op amps operated in a linear feedback circuit or with relaxation oscillator circuits operated in a manner well known to those of skill in designing capacitance measuring circuits. The capacitance measured by the control module can be used by the module to control the heating of the oxygen sensor as explained fully below. Programming of the control module to accomplish the measurement, monitoring, and control functions can be done in normal manner by those of skill in the art of programming such devices.

Figure 2:
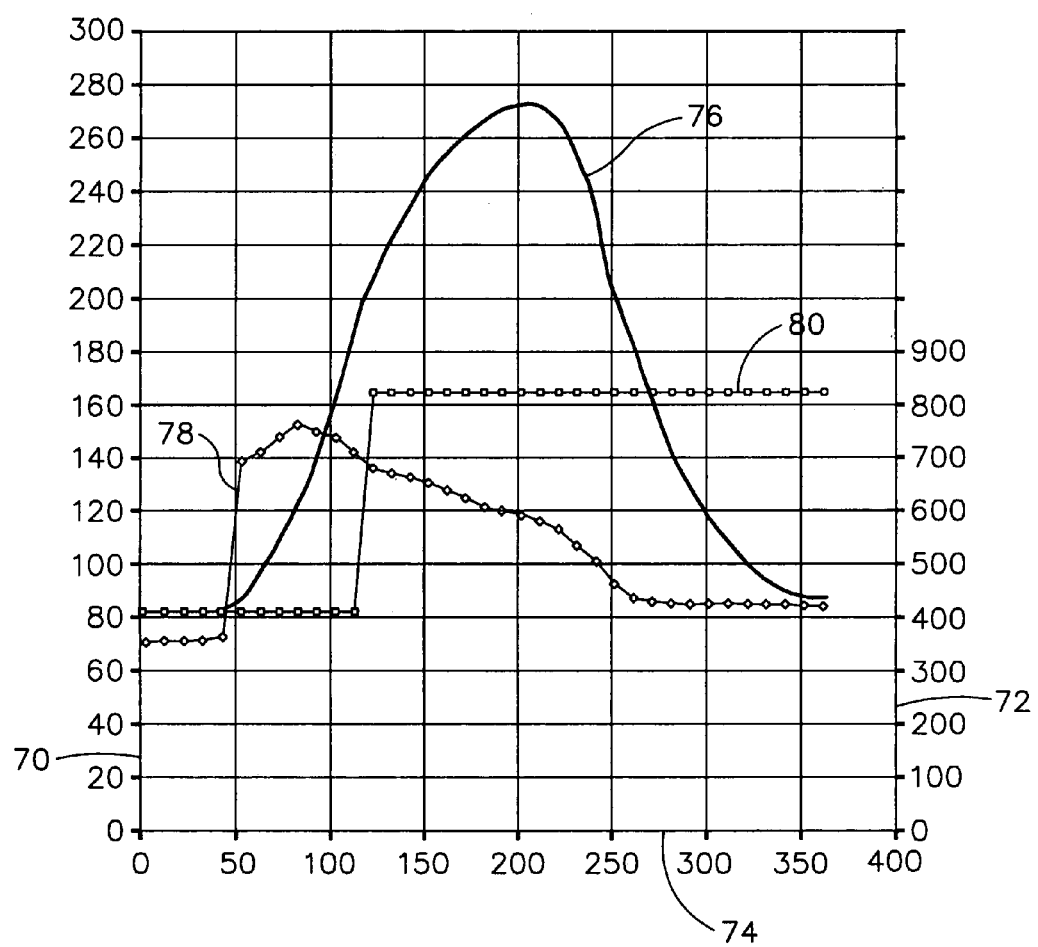
FIG. 2 graphically illustrates capacitance of an oxygen sensor and heater rod response under various operating conditions.

FIG. 2 illustrates graphically the measured capacitance of a representative oxygen sensor under various operating conditions. Also illustrated is oxygen sensor heater temperature as controlled in accordance with an embodiment of the invention. Vertical axis 70 indicates measured capacitance in nanofarads (nF), vertical axis 72 indicates heater temperature in degrees Celsius (° C.), and horizontal axis 74 indicates elapsed time in seconds after cold engine start up. Curve 76 illustrates measured capacitance of a Denso Super Quick (9W) oxygen sensor located in a post catalytic converter position on a motor vehicle. The capacitance was measured with no power applied to the heater rod of the oxygen sensor, i.e., the heater rod was not heating the oxygen sensor. The ambient temperature was less than 5° C., a temperature less than the dew point. The measured capacitance was initially about 70 nF (some portion of which may be circuit capacitance) and rose to about 270 nF as water vapor in the exhaust condensed between the outer electrode and the shell of the oxygen sensor. After reaching a maximum measured capacitance after about 200 seconds, the capacitance began to drop as the oxygen sensor was heated by the exhaust gases and the condensed water was vaporized.

Curve 78 illustrates capacitance of an oxygen sensor operated in accordance with an embodiment of the invention. Curve 80 illustrates the temperature of the heater rod of the oxygen sensor as the oxygen sensor is operated in accordance with the embodiment of the invention. Again, the measured capacitance is initially about 70 nF. The heater is initially operated at a restricted heater temperature, for example at a temperature about one half of the normal operating temperature. Operating the heater at the restricted temperature, as opposed to delaying all power to the heater, helps to reduce the amount of liquid water inside the oxygen sensor. The restricted temperature helps to vaporize the liquid water, but does not thermally shock the oxygen sensor. As with the heater off situation, as illustrated by curve 76, the measured capacitance begins to rise after about 50 seconds of engine operation as liquid water condenses on the elements of the oxygen sensor. In accordance with an embodiment of the invention, both the absolute value of the measured capacitance and the rate of change in capacitance are monitored by the control unit. Based on the measured capacitance and the rate of change of capacitance, the heater temperature is increased to the normal operating temperature of about 820° C. at the earliest possible time after engine start up consistent with safely operating the oxygen sensor as explained more fully below. That is, the heater is powered to normal operating temperature as soon as practical so that the oxygen sensor can be fully functional in measuring exhaust gas oxygen as an aid in controlling engine operating conditions to minimize emissions and to maximize fuel efficiency. Full power is not applied to the heater rod to raise the heater to the normal operating temperature, however, until the measured capacitance and rate of change in capacitance indicate that the heater temperature can be increased without risk of thermal shock damage to the oxygen sensor.

Figure 3:
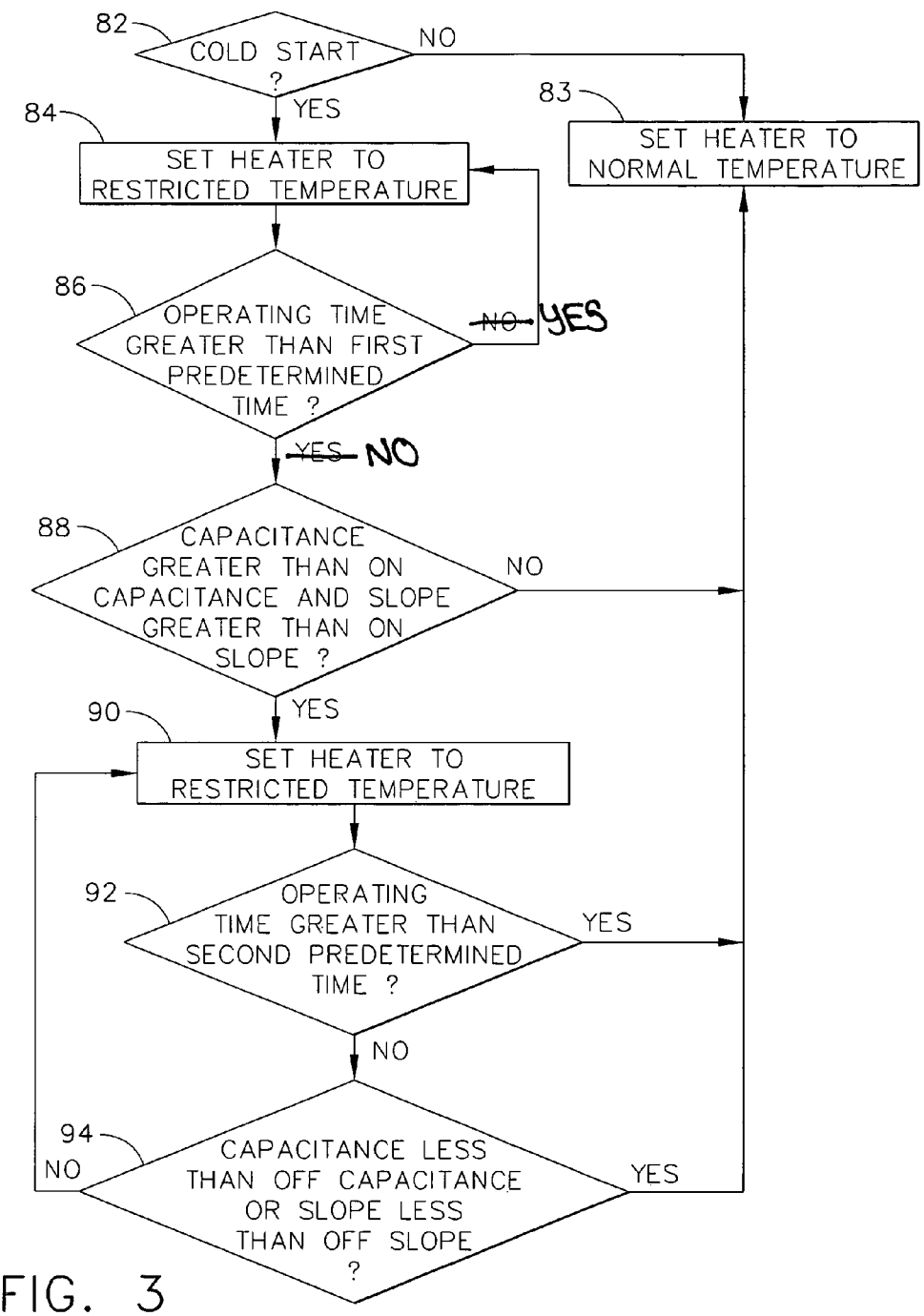
FIG. 3 illustrates, in flow chart format, a method for controlling the heating of an oxygen sensor in accordance with an embodiment of the invention.

FIG. 3 illustrates, in flow chart format, a method for controlling the heating of an oxygen sensor in accordance with one embodiment of the invention. The process illustrated in FIG. 3 is implemented, for example, by a control module coupled to an oxygen sensor in the manner illustrated in FIG. 1. Initially the control module measures engine temperature and senses whether or not the vehicle engine is being started from a cold start (step 82). If the start is not a cold start, that is, the engine is being restarted and is already at a safe operating temperature, the control module controls the level of power applied to the heater rod and causes the heater rod of the oxygen sensor to be heated to the normal, full heater temperature (step 83). A safe operating temperature is a temperature at which the exhaust system is sufficiently heated so that water vapor will not condense on the oxygen sensor and cause thermal shock damage. The normal, full heater temperature is, for example, a temperature greater than about 600° C., and preferably is a temperature of about 820° C. The control module also begins to monitor engine operating time and the capacitance and rate of change of capacitance (slope) as measured between the oxygen sensor outer electrode and shell.

If the control module senses that the vehicle engine is being started from a cold start, the module controls the level of power applied to the heater rod to cause the heater rod of the oxygen sensor to be heated to a restricted temperature (step 84). For example, the heater rod can be heated to a temperature lower than the normal, full operating temperature, such as a temperature of about one half the normal, full operating temperature.

The control module continues to monitor engine operating time. If the engine operating time is less than a predetermined initial operating time, the control module maintains the power applied to the heater rod to maintain the heater rod at the restricted heater temperature (step 86) regardless of measured capacitance or capacitance slope. The predetermined initial operating time can be, for example, a time of about 75 seconds. If the engine operating time exceeds the predetermined initial operating time, the control module compares the measured capacitance and capacitance slope, as measured between the outer electrode and the shell of the oxygen sensor, to a predetermined capacitance on value and to a predetermined capacitance on slope, respectively (step 88). The predetermined values for capacitance on value and capacitance on slope are highly dependent on the particular oxygen sensor being used as well as the configuration of the leads coupling the sensor to the control module and to the system for measuring capacitance employed by the control module. In accordance with one particular embodiment of the invention, the predetermined capacitance on value can be about 100 nF and the capacitance on slope can be about 2 nF/second. If the measured capacitance is greater than the predetermined capacitance on value and the measured capacitance slope is greater than the predetermined capacitance on slope, the control module maintains the oxygen sensor heater rod at the restricted heater temperature (step 90). If the measured capacitance is not greater than the predetermined on capacitance or the measured capacitance slope is not greater than the predetermined capacitance on slope, the control module causes the power to the heater rod to be increased, causing the oxygen sensor heater rod to be heated to the normal, full operating temperature (step 83).

The control module continues to monitor the engine operating time (step 92). If the engine operating time exceeds a predetermined extended operating time, the control module causes the power to the heater rod to be increased, causing the oxygen sensor heater rod to be heated to the normal, full operating temperature (step 83). The predetermined extended operating time can be a time such as about 600 seconds. If the engine operating time does not exceed the predetermined extended operating time, the control module compares the measured capacitance and capacitance slope to a predetermined capacitance off value and to a predetermined capacitance off slope, respectively (step 94). The predetermined capacitance off value and the predetermined capacitance off slope are highly dependent on the particular oxygen sensor being used as well as the configuration of the leads coupling the sensor to the control module and to the system for measuring capacitance employed by the control module. In accordance with one particular embodiment of the invention, the predetermined capacitance off value can be about 120 nF and the capacitance off slope can be about −0.5 nF/second. If the measured capacitance is less than the predetermined capacitance off value or the measured capacitance slope is less than the predetermined capacitance off slope, the control module maintains the oxygen sensor heater rod at the normal heater temperature (step 83).

In accordance with one embodiment of the invention, the process illustrated in FIG. 3 can be applied in a development environment to calibrate and set a control module. Engine temperature, ambient temperature, engine operating time, and capacitance and capacitance slope, as measured between the outer electrode and the shell of an oxygen sensor, can be monitored for each configuration of a test oxygen sensor, vehicle model, engine, and exhaust system under different ambient conditions. The monitored values can be used to model the performance of the particular configuration, and the model can be used to preset the control module to control the pattern of power applied to a heater rod of an oxygen sensor to be mounted in a motor vehicle having the test configuration. In the development environment, the monitoring of the various parameters need not necessarily be carried out by the control module. Instead, the monitoring can be carried out by conventional laboratory measuring equipment.

In accordance with a further embodiment of the invention, each vehicle is equipped for on board detection of the operating parameters. For example, the vehicle is equipped with an oxygen sensor coupled to a control module and the control module is configured to make the necessary capacitance and capacitance slope measurements as described above. The control module thus is able to carry out the steps such as those illustrated in FIG. 3, not in a preset manner, but in a continuous manner during vehicle operation.

While a limited number of exemplary embodiment have been presented in the foregoing detailed description of the invention, it should be appreciated that a vast number of variations exist. It should also be appreciated that the exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

The invention claimed is:

1. A method for controlling the heating of an oxygen sensor mounted in an engine of motor vehicle comprising the steps of:
   detecting starting of the engine;
   measuring capacitance between two elements of an oxygen sensor to determine the presence of a liquid; and
   applying power to a heater of the oxygen sensor in response to the measured capacitance.

2. The method of claim 1 wherein the step of measuring capacitance comprises the step of measuring the capacitance between an electrode of the oxygen sensor and a shell of the oxygen sensor.

3. The method of claim 1 wherein the step of applying power comprises the step of applying a first level of power to the heater if the capacitance is greater than a first predetermined capacitance value and the rate of change of measured capacitance is greater than a first predetermined rate.

4. The method of claim 3 wherein the step of applying power further comprises the step of applying a second level of power greater than the first level of power to the heater if the capacitance is not greater than the first predetermined capacitance value or the rate of change of measured capacitance is not greater than the first predetermined rate.

5. The method of claim 3 wherein the step of applying power further comprises the step of applying a second level of power greater than the first level of power to the heater if the capacitance is less than a second predetermined capacitance value greater than the first predetermined capacitance value and the rate of change of measured capacitance is less than a second predetermined rate, the second predetermined rate less than the first predetermined rate.

6. The method of claim 1 further comprising the steps of:
measuring elapsed time after the step of detecting starting of the engine; and
applying power to the heater at a first power level in response to the measured elapsed time being less than a first predetermine value.

7. The method of claim 6 further comprising the step of increasing the power applied to the heater to a second power level greater than the first power level in response to the measured elapsed time being greater than a second predetermined time, the second predetermined time being greater than the first predetermined time.

8. A method for controlling the heating of an oxygen sensor mounted in an engine of motor vehicle comprising the steps of:
detecting starting of the engine;
measuring capacitance between two elements of an oxygen sensor;
applying power to a heater of the oxygen sensor in response to the measured capacitance;
providing a heater rod operatively coupled to the oxygen sensor;
providing a case coupled to the oxygen sensor for insertion in a motor vehicle;
measuring the capacitance between the outer electrode and the case of a test sensor mounted in a motor vehicle as a function of operating conditions of the motor vehicle;
determining heater rod temperature settings in response to the capacitance measured; and
programming a control unit of a motor vehicle in which an oxygen sensor is to be installed to supply heater power to the heater rod of the oxygen sensor to achieve the determined heater rod temperature settings.

9. The method of claim 8 wherein the step of determining heater rod temperature settings comprises the step of selecting a first heater rod temperature setting for a first temperature in response to measuring a capacitance greater than a first predetermined capacitance and a rate of change of capacitance greater than a first predetermined rate.

10. The method of claim 9 wherein the step of determining further comprises the step of selecting a second heater rod temperature setting for a second temperature greater than the first temperature in response to not measuring both a capacitance that is greater than the first predetermined capacitance and a rate of change of capacitance greater than the first predetermined rate.

11. The method of claim 9 wherein the step of determining further comprises the step of selecting a second heater rod temperature setting for a second temperature greater than the first temperature in response to measuring a capacitance less than a second predetermined capacitance or a rate of change of capacitance less than a second rate.

12. The method of claim 8 wherein the step of programming the control unit further comprises the step of programming the control unit to supply a first power level to the heater rod to achieve a first heater rod temperature for a first predetermined motor vehicle operating time.

13. The method of claim 12 wherein the step of programming the control unit further comprises the step of programming the control unit to supply a second power level to the heater rod to achieve a second heater rod temperature greater than the first heater rod temperature in response to the motor vehicle operating time exceeding a second predetermined time.

14. A method for measuring oxygen levels in exhaust gases of a motor vehicle:
providing an oxygen sensor;
providing a heater rod coupled to the oxygen sensor;
providing an outer electrode surrounding the heater rod;
providing a shell surrounding the outer electrode and configured for mounting the oxygen sensor in the motor vehicle;
providing a first electrode coupled to the outer electrode and a second electrode coupled to the shell, the first and second electrodes configured to facilitate measurement of capacitance between the outer electrode and the shell to determine a presence of a liquid during operation of the motor vehicle.

15. A method for controlling the heating of an oxygen sensor comprising an electrode mounted in an engine of motor vehicle comprising the steps of:
detecting starting of the engine;
measuring capacitance between two elements of an oxygen sensor
applying power to a heater of the oxygen sensor in response to the measured capacitance;
providing a heater rod coupled to the oxygen sensor;
providing a shell coupled to the heater rod;
measuring a vehicle temperature;
setting a power level of heater power delivered to the heater rod at a first level in response to the measured vehicle temperature being below a predetermined temperature;
measuring capacitance and rate of change of capacitance between the electrode and the shell;
maintaining the power level at the first level in response to the measured capacitance being greater than a first predetermined capacitance level and the rate of change of measured capacitance being greater than a first predetermined rate of change; and
increasing the power level of heater power delivered to the heater rod to a second level greater than the first level in response to the measured capacitance being less than a second predetermined capacitance level and the rate of change of measured capacitance being less than a second predetermined rate of change.

16. The method of claim 15 further comprising the step of measuring the time elapsed following a vehicle start and maintaining the power level at the first level in response to the measured elapsed time being less than a first predetermined time.

17. The method of claim 16 further comprising the step of increasing the power level of heater power delivered to the heater rod to the second level in response to the measured elapsed time being greater than a second predetermined time regardless of the measured capacitance or rate of change of capacitance.

18. A method for controlling the heating of an oxygen sensor mounted in an engine of a motor vehicle, the oxygen sensor comprising an oxygen sensing element, a heater, and a surrounding shell, the method comprising the steps of:
measuring capacitance between the oxygen sensing element and the surrounding shell to determine a presence of a liquid; and
applying power to the heater in response to the measured capacitance.

* * * * *